(12) United States Patent
Kuo

(10) Patent No.: US 9,492,243 B2
(45) Date of Patent: Nov. 15, 2016

(54) DENTAL IMPLANT POSITIONING

(75) Inventor: Eric E. Kuo, Foster City, CA (US)

(73) Assignee: Align Technology, Inc., San Jose, CA (US)

( * ) Notice: Subject to any disclaimer, the term of this patent is extended or adjusted under 35 U.S.C. 154(b) by 1189 days.

(21) Appl. No.: 12/154,526

(22) Filed: May 23, 2008

(65) Prior Publication Data

US 2009/0291407 A1 Nov. 26, 2009

(51) Int. Cl.
*A61C 3/00* (2006.01)
*A61C 1/08* (2006.01)
*A61C 7/08* (2006.01)
A61C 8/00 (2006.01)
A61C 13/107 (2006.01)

(52) U.S. Cl.
CPC .............. *A61C 1/084* (2013.01); *A61C 7/08* (2013.01); *A61C 8/008* (2013.01); *A61C 13/0001* (2013.01)

(58) Field of Classification Search
CPC .................. A61C 1/082–1/085; A61C 7/08
USPC .............. 433/6, 18, 24, 215, 172–176
See application file for complete search history.

(56) References Cited

U.S. PATENT DOCUMENTS 5,975,893 A * 11/1999 Chishti et al. .............. 433/6
2004/0170941 A1 * 9/2004 Phan et al. .................. 433/6
2004/0219479 A1 * 11/2004 Malin et al. ............... 433/75
2005/0037320 A1 * 2/2005 Poirier ...................... 433/173
2006/0194163 A1 * 8/2006 Tricca et al. ............... 433/24

OTHER PUBLICATIONS

T.P. Rose et al., The Role of Orthodontics in Implant Dentistry, Dec. 23, 2006, British Dental Journal, vol. 201 No. 12, pp. 753-764.*
Wong et al., "Computer-aided design/computer-aided manufacturing surgical guidance for placement of dental implants: Case report," Implant Dentistry, Sep. 2007 16(3): 123-30.
Sarment et al., "Accuracy of implant placement with a stereolithographic surgical guide," Int J Oral Maxillofac Implants, 2003; 18:571-577.
Di Giacomo et al., "Clinical application of stereolithographic surgical guides for implant placement: Preliminary results," J Periodontol. 2005; 76:503-507.

* cited by examiner

*Primary Examiner* — Matthew Nelson
(74) *Attorney, Agent, or Firm* — Brooks, Cameron & Huebsch, PLLC

(57) ABSTRACT

Methods, devices, systems, and series of appliances are provided for dental implant positioning. One method for positioning an implant with dental treatment includes determining an implant location based on a virtual model of an optimized dental occlusion, moving one or more teeth using a first number of a series of dental appliances, from a first orientation to a second orientation, the second orientation exposing the implant location, placing an implant at the exposed implant location using a landmark included in at least one of the series of dental appliances, repositioning one or more teeth using a second number of the series of dental appliances, from the second orientation to a successive orientation.

28 Claims, 8 Drawing Sheets

DENTAL IMPLANT POSITIONING

BACKGROUND

The present disclosure is related generally to the field of dental treatments. More particularly, the present disclosure is related to using a dental positioning appliance to facilitate dental implant positioning.

Some dental processes use positioning appliances for realigning teeth. Such appliances may utilize a thin shell of material having resilient properties, referred to as an "aligner", which generally conforms to a patient's teeth but is slightly out of alignment with the initial tooth configuration.

Placement of such an appliance over the teeth provides controlled forces in specific locations to gradually move the teeth into a new configuration. Repetition of this process with successive appliances that provide progressive repositioning may eventually move the teeth through a series of intermediate arrangements to a final desired arrangement, which then may allow positioning of the dental implant to occur at that time.

Some dental treatments involve a combination of repositioning misaligned teeth and insertion of a dental implant for improved cosmetic appearance and/or dental function. Repositioning of teeth may result from inadequate space to access a desired implant position and/or a desire to provide an improved position for placement of the implant by aligning neighboring teeth.

Repositioning may be accomplished, for instance, by applying orthodontic forces to one or more teeth over a period of time. This may be performed, in some instances, by first aligning the teeth using dental braces, and then placing the implant when the desired implant position has been adequately prepared.

This approach may be beneficial in many instances. However, such a dental treatment sequence may prolong the therapeutic regimen by waiting until dental realignment is complete before initiating positioning of the implant. Potential drawbacks also may include compromised smile appearance when the implant position is in an anterior region of the mouth and/or risks known to be associated with treatments using dental braces, among others.

DETAILED DESCRIPTION

Figures 1A, 1B:
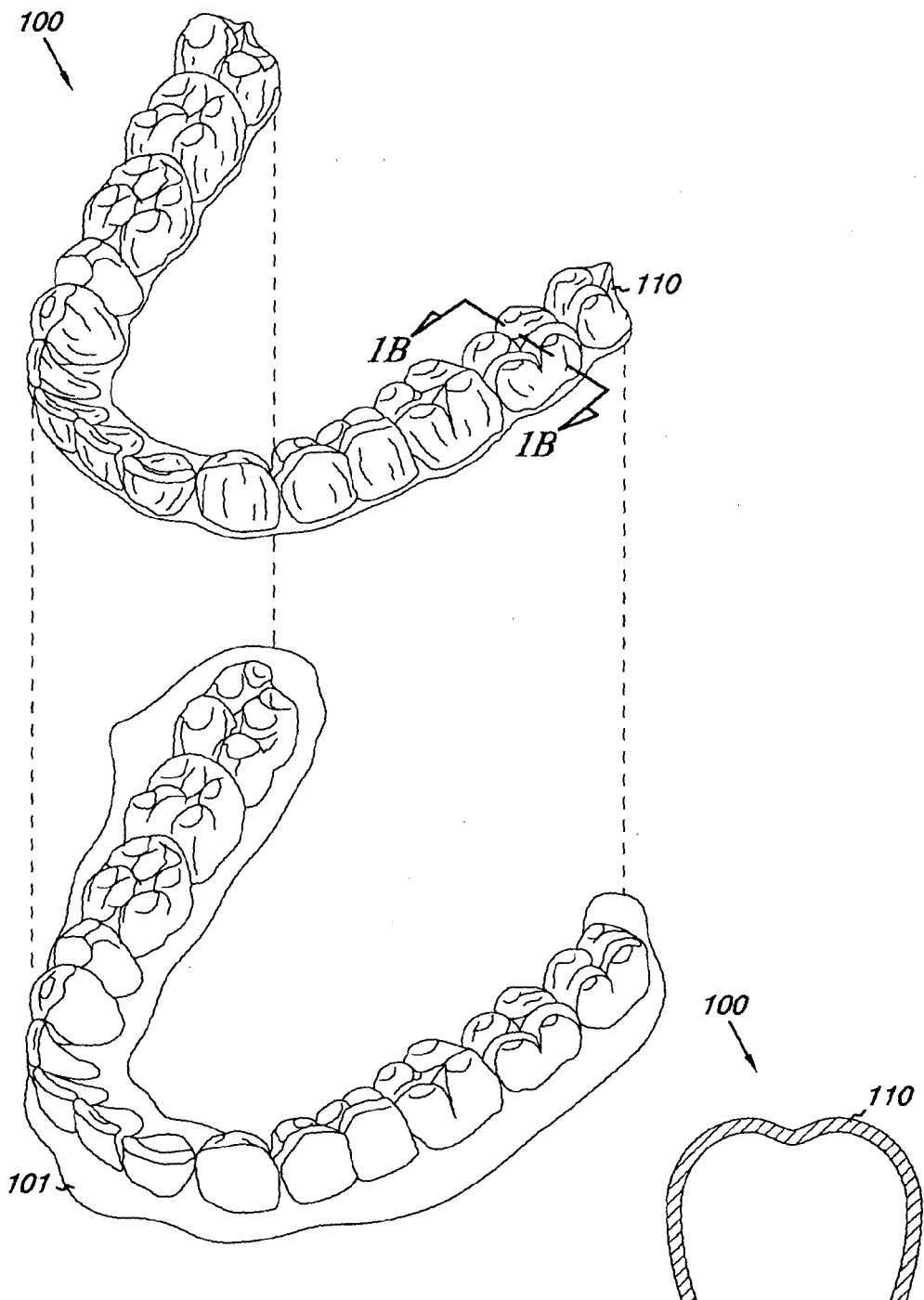
FIG. 1A illustrates a lower jaw of a patient together with an example of a dental positioning adjustment appliance.
FIG. 1B illustrates a cut away view of the appliance of FIG. 1A taken along line 1B-1B.

In some dental procedures, a computerized tomography (CT) scan may be created to define a patient's dentition prior to initiation of dental implant treatment. In some such procedures, a virtual implant may be placed on the scan during the planning process in a simulated implant treatment position to help avoid impingement of the implant on important anatomical structures (e.g., nerves, blood vessels, and/or adjacent tooth roots) and also to plan a desired position of the implant in the bone to improve osseointegration in the actual implant. The virtual implant also may be positioned in a way that provides an implant surgeon and/or dentist improved access to the implant when restoring the implant with a final prosthetic (e.g., a crown, overdenture, etc.).

As used herein, the term implant can include permanent implants or temporary implants (e.g., mini implants or temporary anchorage devices). Positioning of the implant (both virtual and actual) may, however, be compromised when one or more of the patient's teeth are originally in such a position so as to obstruct a desired placement of the implant. For instance, angulation of adjacent teeth to a desired implant position may be such that a line of draw for restoring the implant may compromise the access and/or retention of the prosthesis to the implant.

Another possibility may be that the angulation between the implant and the final restoration is undesirable due to resulting loading characteristics when the implant is restored. A further possibility, among others, is that a bite relationship (e.g., occlusion) between the lower and upper jaw may be such that resulting forces on the placed implant would be unfavorable for long-term success of the implant.

In such instances, the existing positioning of the surrounding teeth (including those in the opposing jaw) may not provide a favorable and/or desirable dental occlusion and/or cosmetic appearance for placement of dental implants. That is, an alternative position of the teeth and/or jaw relationship may provide a more favorable arrangement for successful prognosis for placement of one or more implants. A determination of a more favorable occlusion based on repositioning of tooth arrangement and/or jaw position may enable an improved position of the dental implant, for example, when obstructing and/or interfering teeth are repositioned into the desired position, according to the treatment plan, prior to implant placement.

According to the present disclosure, appliances and methods are provided for positioning an implant with dental treatment by determining an implant location based on a virtual model of an optimized dental occlusion. Among the various embodiments described herein, one or more teeth can be moved using a first number of a series of dental appliances from a first orientation to a second orientation, where the second orientation exposes the implant location, and an implant can be placed at the exposed implant location using a landmark included in at least one of the series of dental appliances. One or more teeth can, in various embodiments, be repositioned using a second number of the series of dental appliances, from the second orientation to a successive orientation.

FIG. 1A illustrates a lower jaw of a patient together with an example of a dental positioning adjustment appliance. As described in the present disclosure, embodiments of dental positioning adjustment appliances, as illustrated in FIG. 1A, can include an appliance 100 made out of a polymeric material 110. However, the appliance 100 made out of the polymeric material 110 is presented by way of example and not by way of limitation.

That is, appliances used for dental positioning adjustment (which, as described in the present disclosure, can be termed "aligners") can be formed using a variety of techniques and remain consistent with the present disclosure. The polymeric material can be a planar sheet of material or strips of material, among other material configurations.

The methods of the present disclosure can employ any positioners, retainers, and/or other removable appliances for finishing and/or maintaining teeth positions in connection with dental treatment. The embodiments of the present disclosure can provide a plurality of such appliances intended, for example, to be worn by a patient successively in order to achieve the gradual tooth repositioning, as described herein.

The appliance 100 can, for example, be formed from a polymeric shell having a cavity shaped to receive and resiliently reposition one or more teeth from one teeth arrangement to a successive teeth arrangement. The polymeric shell may be designed to fit over a number of teeth (e.g., all teeth, as illustrated in FIG. 1A) present in the upper and/or lower jaw 101 of a patient.

In some situations, certain individual and/or sets of teeth can be repositioned while other teeth can provide a base and/or anchor region for holding the repositioning appliance in place as it applies the resilient repositioning force against the tooth or teeth to be repositioned. In complex cases, however, many or most of the teeth will be repositioned at some point during the treatment. In such cases, one or more of the teeth to be moved also can serve as a base and/or anchor region for holding the repositioning appliance.

Additionally, the gums (e.g., the gingiva), the palate, and/or other surrounding tissue can contribute to serving as an anchor region, thus allowing all or nearly all of the teeth to be repositioned at the same time. In some cases, however, individual attachments may be affixed on one or more of the teeth with corresponding receptacles or apertures in the appliance 100, as described in detail in with regard to other figures in the present disclosure.

FIG. 1B illustrates a cut away view of the appliance of FIG. 1A taken along line 1B-1B. The cut away view of the appliance 100 illustrated in FIG. 1B illustrates an embodiment made out of a polymeric material 110 included, for example, in a polymeric shell having a cavity shaped to receive and resiliently reposition one or more teeth from one teeth arrangement to a successive teeth arrangement.

Among the considerations to be resolved following dental treatment as just described may be precisely where to position the implants because, for instance, the CT-aided implant placement determined prior to the dental treatment may not account for tooth movement that occurs during the dental treatment. That is, the CT-aided implant placement may determine an appropriate position for the implants in the current arrangement of the dentition, rather than after repositioning of a number of teeth during the orthodontic dental treatment.

Positioning of dental implants as a surgical procedure after the orthodontic dental treatment may introduce alterations in the dentition position, the root position, and/or the surrounding gingival and/or alveolar bone structure that may affect the prognosis of the subsequent implant placement. Another consideration may be implant treatments being static, for instance, when the implants may be placed on the teeth as they originally reside, when some tooth movement prior to placement of the implant, in some situations, could result in a superior functional and/or aesthetic result.

Figure 2A:
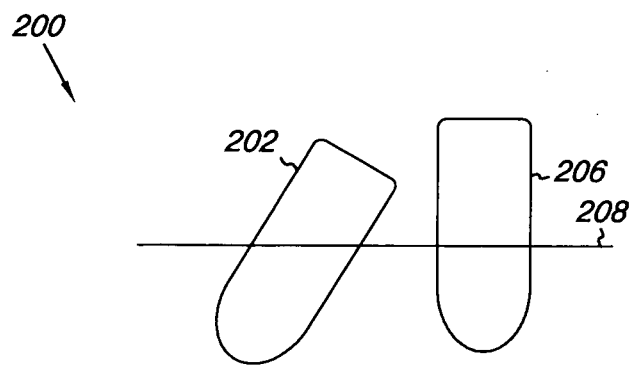
FIG. 2A illustrates an example of misaligned teeth in a lower jaw of a patient with inadequate space for a final restoration supported by a dental implant.

FIG. 2A illustrates an example of misaligned teeth in a lower jaw of a patient with inadequate space for a final restoration supported by a dental implant. The example of misaligned teeth 200 illustrated in FIG. 2A shows one improperly oriented tooth 202 adjacent to one substantially properly oriented tooth 206. The one improperly oriented tooth 202 and the one substantially properly oriented tooth 206 are shown to be positioned in a substrate 208 that can, in various embodiments, represent a gum line or a jaw bone.

The example illustrated in FIG. 2A shows a vacancy between the one improperly oriented tooth 202 and the one substantially properly oriented tooth 206, which can, in various embodiments, be filled by a dental implant and attached to an associated prosthetic dental restoration following realignment of the two teeth 202, 206. Alternatively, a pontic (e.g., a fake tooth) may temporarily be built and/or inserted to fill the space while the dental implant is integrating into the bone. Once the implant is ready to receive the final prosthesis, the pontic may be removed and/or replaced with the final restorative prosthesis by attaching the final restorative prosthesis to the implant.

As appreciated by one of ordinary skill in the relevant art, illustrations in the present disclosure showing a limited number of (e.g., one or two) teeth, implants, and/or pontics are shown for clarity and not by way of limitation. That is, the present disclosure is meant to cover repositioning of one or more misaligned teeth and/or placement and/or positioning of one or more dental implants.

Figure 2B:
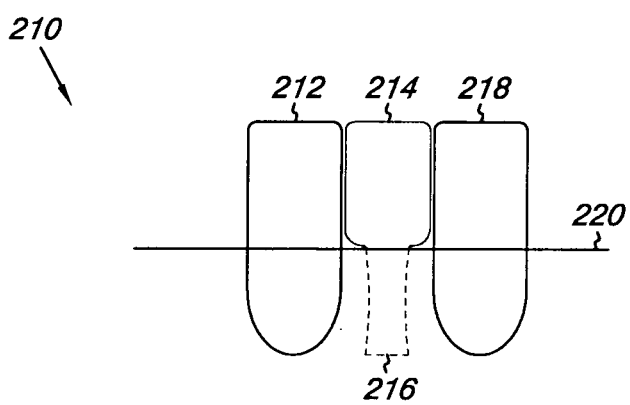
FIG. 2B illustrates an example of aligned teeth in a lower jaw of a patient between which a dental implant has been positioned.

FIG. 2B illustrates an example of aligned teeth in a lower jaw of a patient between which a dental implant has been positioned. The example of aligned teeth 210 illustrated in FIG. 2B shows a first substantially properly oriented tooth 212 adjacent to a prosthetic dental restoration 214 (e.g., a temporary pontic) attached to an implant mount 216, which is adjacent to a second substantially properly oriented tooth 218. The first and second substantially properly oriented teeth 212, 218 are shown to be positioned in a substrate 220 that can, in various embodiments, represent a gum line of a jaw structure.

The example illustrated in FIG. 2B shows that a vacancy between the first and second substantially properly oriented teeth 212, 218 can, in various embodiments, be filled by the prosthetic dental restoration 214 and/or the implant mount 216, for example, following creation of space between the two misaligned teeth 202, 206 illustrated in FIG. 2A. As such, FIG. 2B can, in various embodiments, illustrate a virtual treatment plan incorporating dental treatment, implant placement, and/or a final restoration design.

Figure 2C:
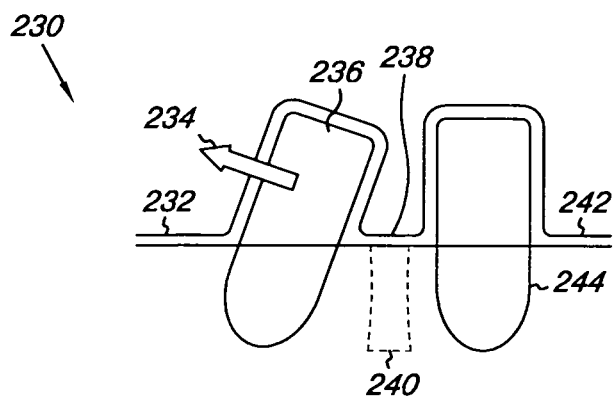
FIG. 2C illustrates a cut away view of an example of a dental positioning adjustment appliance embodiment according to the present disclosure.

FIG. 2C illustrates a cut away view of an example of a dental positioning adjustment appliance embodiment according to the present disclosure. The example of creation of space for positioning an implant 230 illustrated in FIG. 2C shows an embodiment of a dental positioning adjustment appliance 232 (e.g., an aligner) functioning to reposition 234 one improperly oriented tooth 236.

Repositioning the improperly oriented tooth 236 can, in various embodiments, allow creation of space 238 sufficient to insert and/or properly position an implant 240 between the improperly oriented tooth 236 and a substantially properly oriented tooth 244. A portion of the aligner 242 associated with a substantially properly oriented number of teeth can, in various embodiments, serve as an anchor for initially and/or continuously repositioning the improperly oriented tooth 236. The portion of the aligner 242 also can maintain the position of tooth 244 while tooth 236 is being moved.

In various embodiments as described in the present disclosure, an aligner can be designed to include an implant positioning guide. The aligner also can, in various embodiments, include an "offset" portion (e.g., area and/or volume) separating the aligner a distance from the implant and/or surrounding tissue to allow the implant to osseointegrate without occlusal pressure while the remaining dental treatment is being completed. Hence, the implant can be placed while the dental treatment is continuing, rather than at the end of the dental treatment.

The aligner also can be designed to include one or more fake teeth (e.g., pontics) that are temporarily used to aesthetically camouflage the edentulous (i.e., toothless) region while the tissue around the implant is healing. A number of pontics, for example, can be used as temporary "try-ins" to assist in enabling patient satisfaction with planning of tooth shade, shape, and/or position, among other characteristics, prior to placement of a more permanent final restoration. With these features, the implant can be placed while the orthodontic treatment is continuing, rather than at the end of the orthodontic treatment, while aiding in patient satisfaction with appearance during the process.

A dental treatment plan as described in the present disclosure can, in various embodiments, include three-dimensional (3-D) digital scanning of the patient's dentition. This can be accomplished a number of ways, for example, CT scanning, magnetic resonance imaging (MRI) scanning, light scanning, destructive scanning, and/or laser scanning, among other scanning technologies. In some embodiments, the patient's jaw and/or soft tissue structure can be scanned using, for example, CT scanning, and/or MRI scanning, among other scanning technologies.

Hybrid scanning technology also can be used, whereby general anatomical structures are identified using direct patient scanning (e.g., CT and/or MRI) and more accurate surface details are imaged using direct light and/or dental impression/model scans, with the multiple scans merged together via landmark superimposition to create a final working scan. In such embodiments, the 3-D dentition structure scan can be superimposed over the 3-D scan of the patient's jaw and/or soft tissue structure. This can be accomplished using various shape matching algorithms (e.g., AST matching as described in a number of published applications and/or issued patents assigned to Align Technology, Inc.).

A hybrid scan as just described may capture high accuracy surface detail images of the dentition without exposing the patient to unnecessarily high amounts of ionizing radiation. This methodology may also overcome inaccuracy problems associated with radiation scatter that can occur when scanning metal objects, such as dental fillings and/or prostheses containing metal (e.g., dental crowns and/or bridges, among others).

Such a superimposition can result in a high resolution 3-D dentition model matched to the patient's dental roots, tissues, jaw bones, nerves, and/or other soft and hard tissue features (e.g., jaw muscles, tongue, cheek, and/or facial attributes) that can be used as substantially fixed markers. The high resolution 3-D model of the teeth and/or associated structures can be utilized for planning of the final dental alignment and/or occlusion prior to starting treatment. The high resolution 3-D model of the teeth and/or associated structures also can be utilized for planning of implant placement and/or positioning prior to starting treatment.

In some embodiments, virtual final restorations (e.g., including the crowns that are to be placed) can be created to determine favorable and/or desirable positioning of the final prosthesis on top of the implants and/or improve occlusion against teeth of an opposing arch after the dental therapy is completed. Individual virtual teeth can be moved to a number of positions in consideration of the desired implant placement. One or more virtual implants are created and positioned relative to the 3-D fixed markers. The virtual teeth, aligners, virtual implants, and/or virtual restoration may be repositioned in an iterative fashion before settling on a desired dental treatment plan.

Dental movement of improperly oriented and/or positioned teeth can, in various embodiments, be parsed into an incremental treatment plan that animates the progression of the virtual teeth from an initial state to a final state. Each step can be calibrated and/or constrained, for example, based on incremental tooth root movement (e.g., no more than 0.25 millimeter (mm) movement per tooth per step), among other methods. In some embodiments, the increments can be evaluated for interdental digital overlaps called "collisions" and these collisions can be resolved such that the teeth can slide past each other during orthodontic dental treatment.

For each incremental movement of treatment, a dental aligner can, in various embodiments, be formed to enable one or more of the patient's teeth to be moved into a geometry corresponding to an interior topology of the aligner (e.g., see FIG. 1B). Once the positioning of the teeth has substantially conformed to the geometry of a preceding aligner, the next aligner in a series of aligners can be worn for a number of hours or weeks of wear to continue progression of tooth movement to a planned final state, for example, as determined by the virtual final restoration plan.

In some instances, such as with traditional orthodontics, the final position of the implant may not be predetermined and the implant may be placed and/or positioned after the orthodontic treatment is completed. Hence, the patient may have to wait a number of months during orthodontic treatment to, for example, expose the favorable and/or desirable implant location, as well as after orthodontic treatment to allow for adequate healing and osseointegration before the patient can have their implant restored with a crown or other prosthesis. In contrast, as described in the present disclosure, at the earliest stage in the dental treatment where a desired implant location is fully accessible (e.g., when movement has progressed sufficiently that no tooth is obstructing the desired target implant location) and stable (e.g., no other teeth are intended to be moved into the implant space), an implant can, in various embodiments, be placed and/or positioned in the desired location while the orthodontic treatment is continuing.

The final position of the implant can be determined digitally in connection with the dental aligner treatment and, when the necessary space has been created by the orthodontic treatment, the implant can be placed and/or positioned while the orthodontic treatment is continuing. Placing and/or positioning the implant during the orthodontic treatment, as opposed to after the orthodontic treatment, may shorten the overall treatment time because the healing period for osseointegration can simultaneously occur while the remaining orthodontic treatment is continuing.

This can reduce the delay in placement of the final restoration (e.g., a crown) once the dental treatment has been completed. By working in parallel, instead of in series, the patient can have ample time for implant osseointegration, and this may allow for an improved prognosis for the health and longevity of the dental implant and/or the health and/or comfort of the patient.

To facilitate the implant placement and/or positioning process, a virtual object can, in various embodiments, be placed at the final planned stage of treatment to indicate a desired position where the implant should be placed. That is, by simulating the orthodontic treatment, on which the aligner topology (e.g., contours) will be based, the implant position can be predetermined and/or identified with a virtual indicator relative to the virtual dentition, which can be transferred to the contours of the actual aligners. During the treatment planning phase, the virtual teeth representing the actual dentition can be set to a position where the implant could be adequately placed without obstruction from the neighboring teeth and in a manner that avoids important anatomical structures (e.g., nerves, vessels, and such).

This position can, for example, provide the earliest time at which the implant can be placed and/or positioned, for instance, so long as no other teeth cross in the path of the implant for the rest of the dental treatment. For example, additional space (e.g., 2 mm) may be desired to allow for an adequate implant space and the additional space can be created in five months with orthodontic treatment, although the entire orthodontic treatment may require an additional twelve months due to the severity of dental misalignment. In such situations, the implant can, as described in the present disclosure, be placed after five months of treatment, thereby allowing seven months of osseointegration time to occur while the remaining orthodontic treatment is ongoing.

As described in the present disclosure, the virtual indicator representing the desired position of the dental implant (e.g., corresponding to the position where the final restoration is to be placed) can be embodied as a cylinder, space, and/or hole that can, in various embodiments, be built and/or formed into the actual aligner to serve as a guide (e.g., landmark) to assist in correct placement and/or positioning of the implant (e.g., which can show a dentist or implant surgeon where to place the implant). In some embodiments, the landmark can be a simple indicator that, for example, when used in conjunction with the CT image, can direct the dentist or implant surgeon to an appropriate general location for the implant. In some embodiments, the landmark can serve as a precise drill guide to enable the proper angulation and/or depth of the implant to be built into the aligner itself.

This positioning feature can, in various embodiments, enable the dentist or implant surgeon to correctly position the implant in the desired target position in light of the possibility that additional orthodontic treatment may continue after the placement of the implant. That is, the most visually "obvious" position at the time of implant placement, without the landmark, may not in fact be the appropriate position when the orthodontic treatment is completed.

Figure 3A:
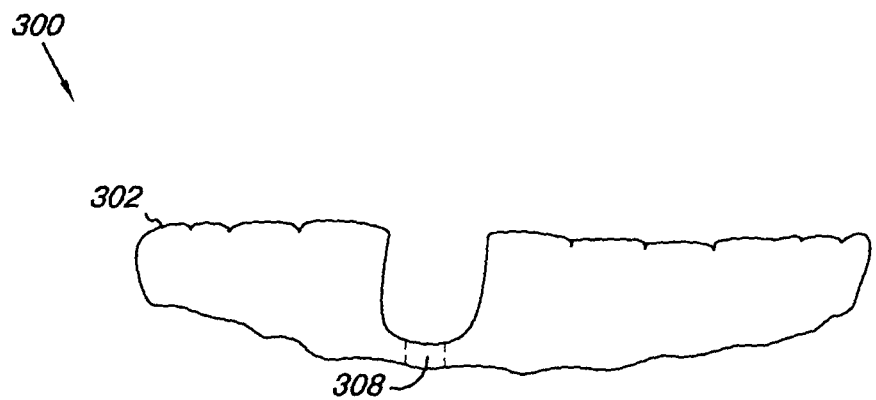
FIGS. 3A-3C illustrate embodiments of dental positioning adjustment appliances usable for dental implant positioning according to the present disclosure.
Figure 3B:
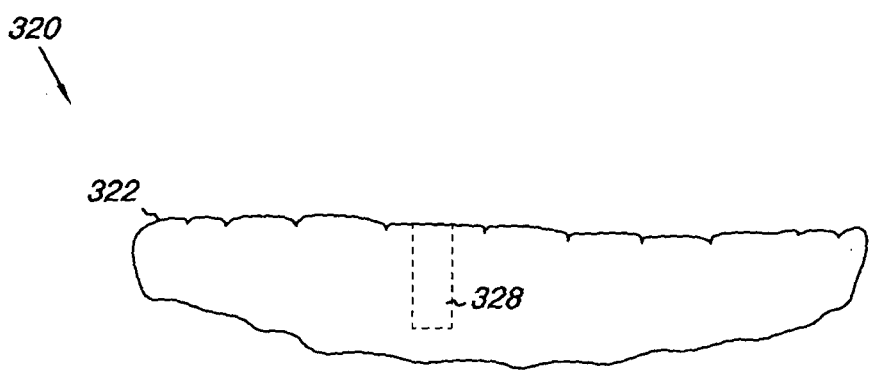
Figure 3C:
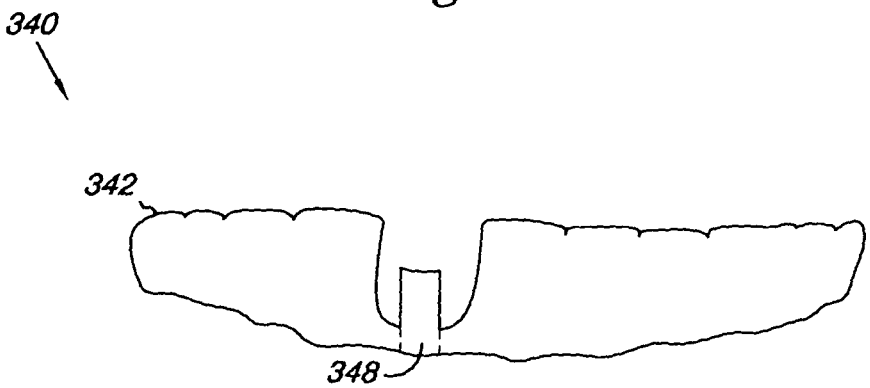

FIGS. 3A-3C illustrate embodiments of dental positioning adjustment appliances usable for dental implant positioning according to the present disclosure. The embodiments of the dental positioning adjustment appliances 300, 320, and 340 illustrated in FIGS. 3A-3C, respectively, show dental aligners formed to include implant placement guides that can, in various embodiments, serve as a landmark for positioning of a dental implant by a dentist or implant surgeon.

FIG. 3A illustrates an example of an embodiment 300 in which the aligner 302 can, in various embodiments, include a perforation 308 (e.g., one or more holes in various shapes through the substance of the aligner). The perforation 308 through the aligner 302 can serve as the implant placement landmark to direct positioning of the implant by a dentist or implant surgeon.

The landmark can, in various embodiments, be used directly as a drill guide, or indirectly as a marking device for a subsequent drill guide. The landmark can, in some embodiments, be used with a separate attachment that serves as a drill guide, whereby the landmark serves, for example, as a receptacle for the attachment.

FIG. 3B illustrates an example of an embodiment 320 in which the aligner 322 can, in various embodiments, include an inset 328 that progresses partially or completely through the substance of the aligner 322 (e.g., one or more insets in various cylindrical or other shapes through the substance of the aligner). The inset 328 illustrated in FIG. 3B can, in some embodiments, be formed as a perforation having longer sides (e.g., a circular wall of a cylinder) than the perforation 308 illustrated in FIG. 3A.

As indicated with regard to FIG. 3A, the landmark illustrated in FIG. 3B can, in various embodiments, be used directly as a drill guide, or indirectly as a marking device for a subsequent drill guide. The landmark can, in some embodiments, be used with a separate attachment that serves as a drill guide, whereby the landmark serves, for example, as a receptacle for the attachment.

The inset 328 illustrated in FIG. 3B can, in various embodiments, be formed in the direction of a desired angulation for the implant. As such, the inset 328 can, in some embodiments, provide wall support to allow tactile feedback for an implant drill, thereby serving as the implant placement guide to direct positioning of the implant by a dentist or implant surgeon. When used as a separate attachment that serves as the guide, the angle of the walls of the guide can correctly position the separate attachment relative to the surrounding teeth and/or oral structures.

FIG. 3C illustrates an example of an embodiment 340 in which the aligner 342 can include an everted cylinder 348 that, in various embodiments, can include a top end of the everted cylinder 348 positioned a fixed distance from a bottom end of the everted cylinder 348 (e.g., one or more everted cylinders in various shapes and/or lengths). The everted cylinder 348 illustrated in FIG. 3C can, in various embodiments, be formed in the direction of a desired angulation for the implant.

Similar to the inset 328 illustrated in FIG. 3B, the everted cylinder 348 illustrated in FIG. 3C can, in various embodiments, provide wall support to allow tactile feedback for the implant drill. Additionally, the everted cylinder 348 can, in various embodiments, allow a drill bit of the implant drill to line up with a wall of the everted cylinder 348 and allow a base of the implant drill to be stopped by the top end of the everted cylinder 348 so that the implant drill bit progresses only a predetermined distance into, for example, the jaw bone of the patient.

That is, the base of the implant drill can be prevented from passing a contact point with the top end of the everted cylinder 348. When the drill guide is a separate attachment, the attachment can, in various embodiments, be coupled to the everted cylinder.

The everted cylinder 348 can, in some embodiments, provide tactile feedback to guide the direction and/or depth of the implant drill, thereby serving as the implant placement guide to direct positioning of the implant by a dentist or implant surgeon. As such, as described with regard to FIGS. 3A-3C, a landmark can be selected from a group that includes a depression, a marking, a hole, a fixture, an inset, and/or a drill guide structure (e.g., an everted cylinder), among other landmark configurations for either direct or indirect guidance for the implant placement.

Figure 4A:
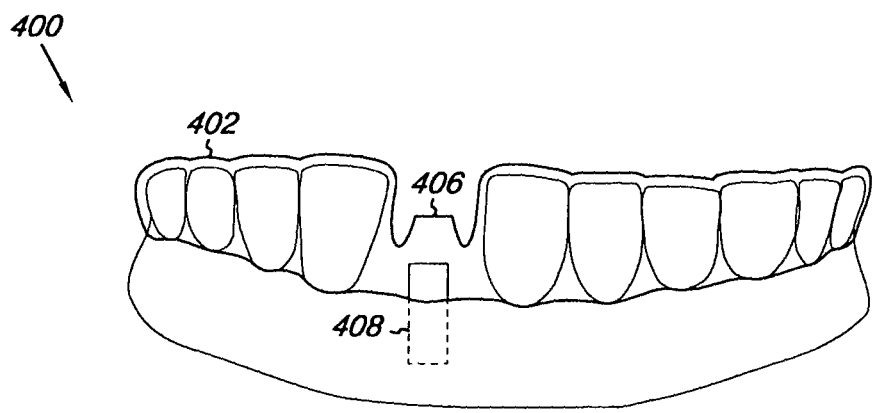
FIGS. 4A-4E illustrate further embodiments of dental positioning adjustment appliances usable for dental implant positioning according to the present disclosure.
Figure 4B:
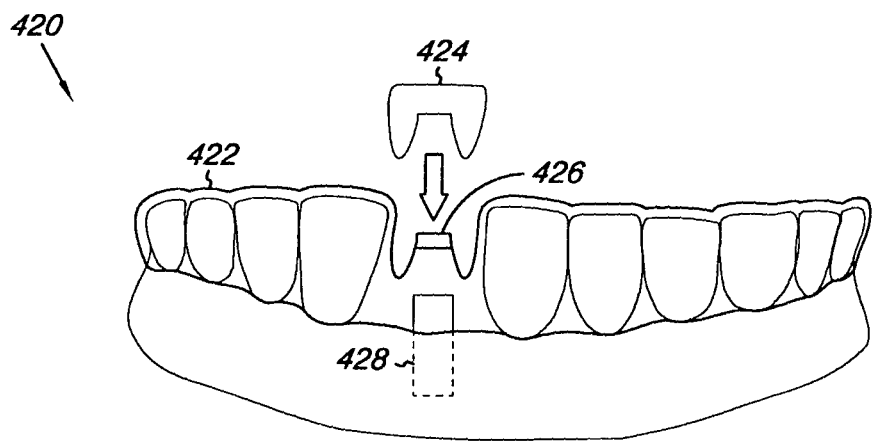
Figure 4C:
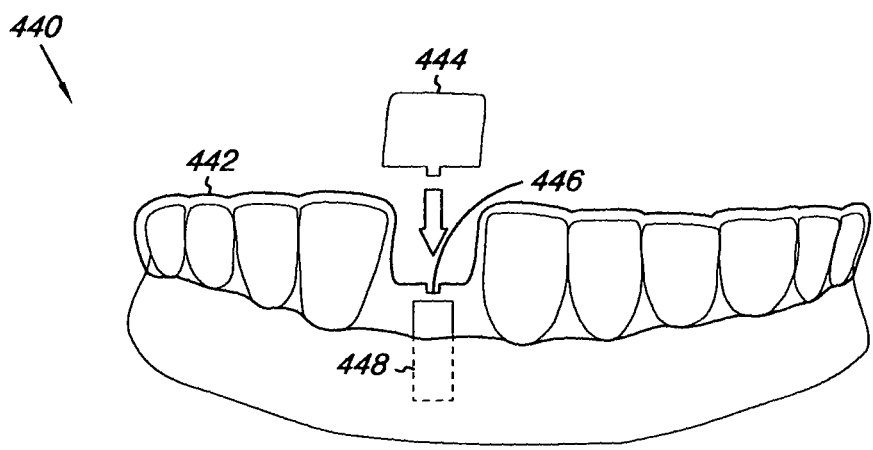

FIGS. 4A-4C illustrate further embodiments of dental positioning adjustment appliances usable for dental implant positioning according to the present disclosure. After an implant has been placed and/or positioned, a dental positioning adjustment appliance (e.g., an aligner) can be applied that is formed with an offset (e.g., reliefs portion).

The offset portion can, in various embodiments, be provided in the aligner so that the aligner does not press on the tissue surrounding the implant. The offset portion can, in various embodiments, be built into the aligner. The three embodiments of the dental positioning adjustment appliances 400, 420, and 440 illustrated in FIGS. 4A-4C, respectively, show dental aligners formed to include offset portions, in various embodiments, although other configurations are covered by the present disclosure.

FIG. 4A illustrates an example of an embodiment 400 in which the aligner 402 can, in various embodiments, include an offset portion 406 (e.g., one or more offset portions in various shapes formed in the substance of the aligner). The offset portion 406 of the aligner 402 can serve to reduce pressure from parts of the aligner 402 on an implant 408 (which can, in various embodiments, include a healing abutment and/or cap) and/or on tissue surrounding the implant.

In many instances, placement of a tooth-like object (e.g., a pontic) on, or creation of a tooth-like object as part of, the aligner may be desirable (e.g., for aesthetic reasons) in combination with the offset feature. In various embodiments, the tooth-like object can be secured as part of the aligner, for example, by forming the aligner and tooth-like object together, by using a geometry built into the aligner as a mating fit to the tooth-like object with a locking mechanism that fits the geometry of the tooth-like object, by designing a tooth-shaped bubble to allow tooth-colored material to be placed into the tooth-shaped bubble, and/or by using a rivet-like system to allow a tooth-like object to be physically snapped onto the aligner without using adhesive substances, among other arrangements.

FIG. 4B illustrates an example of an embodiment 420 in which the aligner 422 can, in various embodiments, include an offset portion (e.g., the offset portion 406 as illustrated in FIG. 4A) to reduce pressure from parts of the aligner 422 on an implant 428 and/or on tissue surrounding the implant. The aligner 422 illustrated in FIG. 4B shows that the aligner 422 can include an abutment geometry 426, in various embodiments, that can enable attachment (e.g., with an adhesive substance, a mechanical connection, etc.) of a tooth-like object 424 (e.g., a pontic) to the abutment geometry 426 and, consequently, to the aligner 422. As such, FIG. 4B illustrates that an aligner can, in various embodiments, be formed with an offset portion and an abutment associated with the offset portion, which can enable attaching, for example, a pontic to the abutment.

FIG. 4C illustrates an example of an embodiment 440 in which the aligner 442 can, in various embodiments, include an offset portion (e.g., the offset portion 406 as illustrated in FIG. 4A) to reduce pressure from parts of the aligner 442 on an implant 448 and/or on tissue surrounding the implant. The aligner 442 illustrated in FIG. 4C shows that the aligner 442 can be formed such that a tooth-like object 444 (e.g., a pontic) can, in various embodiments, be attached to an abutment geometry 446 with a rivet-like connection.

That is, in some embodiments, the tooth-like object 444 can be attached to the abutment 446 without using an adhesive substance. As such, FIG. 4C illustrates that an aligner can, in various embodiments, be formed with an offset portion and an abutment associated with the offset portion, which can enable a rivet-like connection to attach, for example, a pontic to the abutment.

Figure 4D:
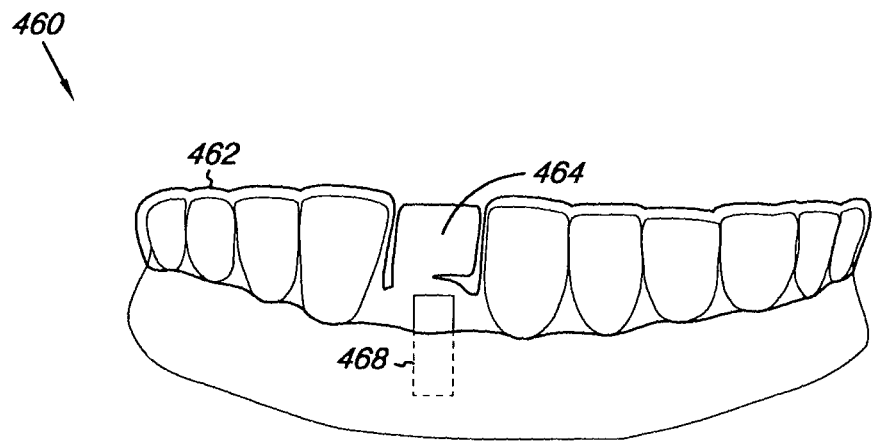

FIG. 4D illustrates an example of an embodiment 460 in which the aligner 462 can, in various embodiments, include an offset portion (e.g., the offset portion 406 as illustrated in FIG. 4A) to reduce pressure from parts of the aligner 462 on an implant 468 and/or on tissue surrounding the implant. The aligner 462 illustrated in FIG. 4D shows that the aligner 462 can be formed such that a tooth-like object 464 (e.g., a pontic) can, in various embodiments, be built into and/or formed as part of the aligner 462.

That is, in various embodiments, both the tooth-like object 464 and the offset can be built into and/or formed from the polymeric material from which the rest of the aligner 462 is formed, although the present disclosure is not limited to using the same material for the tooth-like object 464 and the aligner 462. In some embodiments, the tooth-like object 464 can be formed as a shell of the polymeric material or other suitable material.

In some embodiments, as illustrated in FIG. 4D, the tooth-like object 464 can, in various embodiments, have a notch (or another appropriate weakened arrangement) formed therein to facilitate removal of the tooth-like object 464 in order to access the implant 468 through the offset area or otherwise. As such, FIG. 4C illustrates that an aligner can, in various embodiments, be formed with an offset portion and a tooth-like object associated with the offset portion, which can enable forming the aligner, the offset portion, and the tooth-like object as a single construct.

Figure 4E:
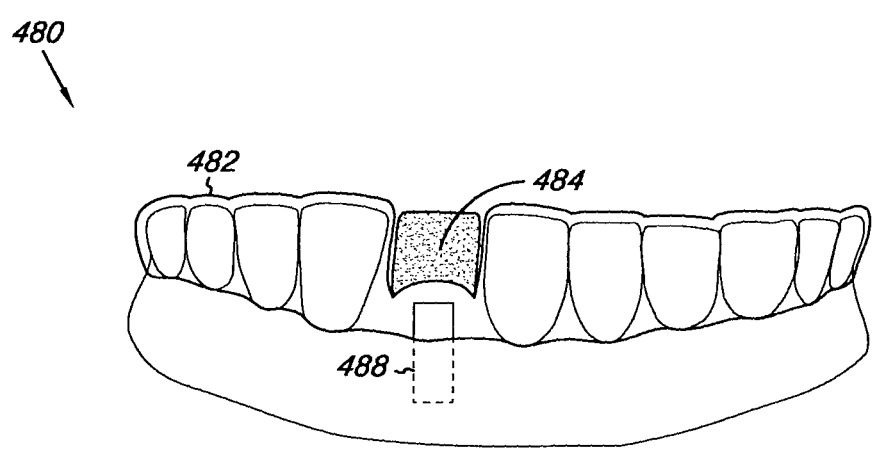

FIG. 4E illustrates an example of an embodiment 480 in which the aligner 482 can, in various embodiments, include an offset portion (e.g., the offset portion 406 as illustrated in FIG. 4A) to reduce pressure from parts of the aligner 482 on an implant 488 and/or on tissue surrounding the implant. The aligner 482 illustrated in FIG. 4E shows that the aligner 482 can be formed such that a tooth-like object 484 (e.g., a pontic) can, in various embodiments, be built into and/or formed as part of the aligner 482, similar to the embodiment 460 illustrated in FIG. 4D.

The embodiment 480 illustrated in FIG. 4E can, in various embodiments, differ from the embodiment 460 in that a portion of the shell can be filled with a solid material (e.g., the polymeric material from which the aligner 482 is formed or otherwise) to make the tooth-like object 484 more substantially solid. In various embodiments, the shell of the tooth-like object 484 can be partially or completely filled with the solid material as long as an offset portion is preserved (e.g., the base of the solid material in the shell becomes the top of the offset portion).

As described with regard to FIG. 4D, both the tooth-like object 484 and the offset illustrated in FIG. 4E can, in various embodiments, be built into and/or formed from the polymeric material from which the rest of the aligner 482 is formed, although the present disclosure is not limited to using the same material for the tooth-like object 484 and the aligner 482. In some embodiments, the tooth-like object 484 can be formed as a shell and/or filler of the polymeric material or other suitable material.

In some embodiments, the tooth-like object, as illustrated in FIGS. 4D and 4E, can be a pontic, in various embodiments, that is built and/or formed from a tooth library and/or a "copy and paste" from another tooth, as will be appreciated by one of ordinary skill in the relevant art. As also will be appreciated by one of ordinary skill in the relevant art, configurations of the embodiments of the aligners, offsets, implants, and/or tooth-like objects illustrated in FIGS. 4A through 4E are simplified for purposes of clarity and are not to be construed as limitations thereof unless explicitly stated as such. For example, the thickness of a layer of polymeric material in an aligner can vary depending upon the positioning and/or application thereof, although such thickness may be represented by a uniformly thin line in FIGS. 4A through 4C.

As will further be appreciated by one of ordinary skill in the relevant art, various features are grouped together in the description of the present disclosure in a single embodiment for the purpose of streamlining the disclosure. This method of disclosure, however, is not to be interpreted as reflecting an intention that the embodiments of the disclosure require more features than are expressly recited in each of the following claims. Rather, as the claim recitations reflect, inventive subject matter lies in less than all features of a single disclosed embodiment.

Hence, predetermining a treatment plan with a virtual model as described in the present disclosure may be a recommended and claimed methodology, however, just forming and/or using an aligner as described in the disclosure and as recited in the following claims is intended as novel subject matter to be protected. For example, novel subject matter as described in the present disclosure can be included in a portion of an aligner, rather than the whole aligner, and remain consistent with the teachings of the present disclosure.

Accordingly, a series of removable dental positioning appliances, as described in the present disclosure, can include, in various embodiments, a first number of aligners for repositioning one or more teeth from a first configuration to a second configuration, and a second number of aligners to reposition one or more teeth from the second configuration to a successive configuration. The repositioning of the one or more teeth to the second configuration can, in various embodiments, expose an implant location space. For example, a series of multiple aligners may be necessary to achieve a desired alignment endpoint configuration. However, the desired alignment endpoint configuration can be planned in the beginning at or near the same point in time as an intermediate alignment configuration (e.g., the second configuration) that allows appropriate implant positioning.

The treatment plan can be revisited, for example, at or near each point in time when an intermediate aligner in the series of aligners is replaced by a successive aligner and altered, if desired, depending upon a level of success achieved. For example, the desired endpoint configuration may be to have a 9 mm width spacing for a single implant. After a succession of 10 aligners, the progress toward the desired endpoint spacing can be measured and, in some instances, another 10 aligners may be prescribed.

After the second 10 aligners have been utilized, progress can be measured again to determine whether the original desired target of 9 mm is realistically attainable. If so, and when necessary, more aligners can be prescribed until the desired spacing is achieved. If the desired spacing of 9 mm appears not to be realistically attainable, an alternative desired spacing can be determined.

The concept of determining an implant position based upon a future position of teeth resulting from orthodontic treatment can be implemented at any point in the series of aligners. That is, when an adequate implant space is achieved, the implant can be placed and/or positioned, even though additional orthodontic treatment is still planned for execution.

In some embodiments, the series of removable dental positioning appliances can, in various embodiments, include one or more aligners including an offset area corresponding to some portion (e.g., area) of the implant location space. In some embodiments, the second number of aligners can, in various embodiments, be configured with either an abutment geometry for attaching a temporary tooth structure in the offset area or a pontic geometry built into the offset area.

In some embodiments, the series of removable dental positioning appliances can, in various embodiments, include successive configurations based on an optimal dental occlusion including a predetermined implant location space. In some embodiments, the series of removable dental positioning appliances can, in various embodiments, include at least one aligner corresponding to the second configuration that can include a guide for implant placement within the implant location space. A configuration for the guide can be, for example, a depression, a marking, a hole, a fixture, an inset, a drill guide mating feature, and/or a drill depth and alignment guide structure, among other configurations.

Accordingly, as described in the present disclosure, a series of dental positioning appliances can be used to expose one or more positions for one or more implants. In various embodiments, a first number of aligners can be used to reposition one or more teeth from a first configuration to a second configuration.

In such embodiments, the one or more teeth that are repositioned to the second configuration expose at least one implant location space. A number of implants can then be placed in the exposed one or more implant location spaces. In some such embodiments, a second number of the series of dental appliances can be used to reposition one or more teeth from the second orientation to a successive orientation.

As described in the present disclosure, at least one of the first number of aligners can include at least one landmark to serve as a guide for placement of an implant. In various embodiments, landmarks can be formed in aligners as one or more of, for example, a depression, a marking, a hole, a fixture, an inset, and/or a drill guide structure in the aligner, among other suitable structures.

In some embodiments, at least one of the second number of aligners can include an offset area corresponding to some portion of the implant location space. At least one of the second number of aligners also can, in various embodiments, include either an abutment geometry to enable attachment of a temporary tooth structure in the offset area and/or a pontic geometry built into the offset area. In some embodiments, the temporary tooth structure attachable in the offset area or the pontic geometry built into the offset area can be at least partially formed from tooth-colored material.

Figure 5:
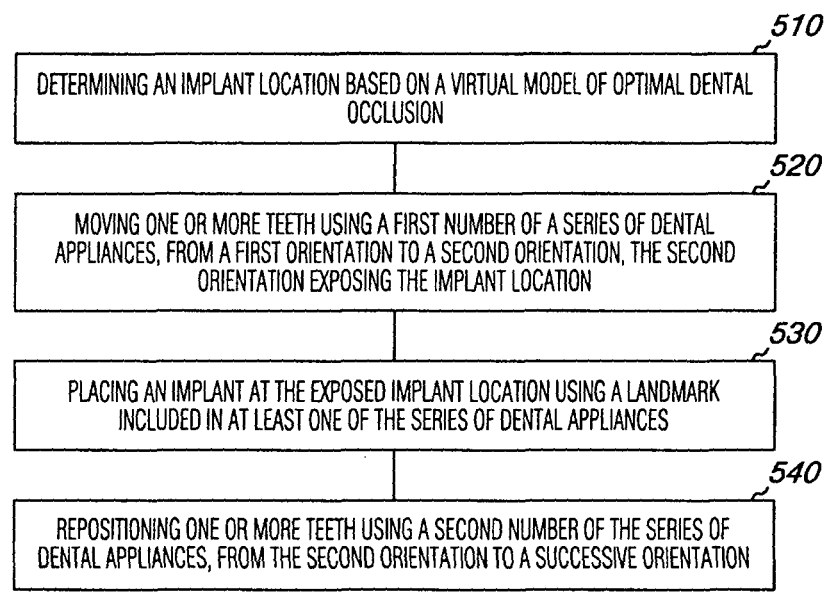
FIG. 5 is a block diagram illustrating a method for positioning an implant with dental treatment according to the present disclosure.

FIG. 5 is a block diagram illustrating a method for positioning an implant with dental treatment according to the present disclosure. Unless explicitly stated, the method embodiments described herein are not constrained to a particular order or sequence. Additionally, some of the described method embodiments, or elements thereof, can occur or be performed at the same, or at least substantially the same, point in time.

The embodiment illustrated in FIG. 5 includes determining an implant location based on a virtual model of an optimized dental occlusion, as shown in block 510. As used in the present disclosure, "optimized dental occlusion" denotes a dental occlusion determined to be favorable and/or desirable by a treatment professional (e.g., a dentist or implant surgeon) with reference to, in some embodiments, a virtual model of dental occlusion that can be either static or dynamic (e.g., that simulates articulation). A dental treatment plan as described in the present disclosure can, in various embodiments, determine the implant location based on the virtual model of optimal dental occlusion through use of 3-D digital scanning of the patient's dentition.

The 3-D digital scanning can be accomplished a number of ways, for example, CT scanning, MRI scanning, light scanning, destructive scanning, and/or laser scanning, among other scanning technologies. In some embodiments, the patient's jaw and/or soft tissue structure can be scanned using, for example, CT scanning, and/or MRI scanning, among other scanning technologies.

In various embodiments, the scanning can include scanning in three dimensions a patient's initial dental anatomy, creating the virtual model of desired dental occlusion based on the patient's dental anatomy, and designing a series of dental appliances (e.g., aligners) where the first orientation is an occlusion of the initial dental anatomy, and the successive orientation is a desired dental occlusion. In some embodiments, the scanning can include digitally scanning a patient's dentition, digitally scanning a dental structure including anatomical features affecting the implant location, and superimposing the dental structure to the dentition of the 3-D patient scan.

As described in the present disclosure, some embodiments of a plan for dental treatment with implant can include creating a virtual model of a number of physical teeth and at least one implant as a virtual tooth, and planning a virtual treatment process including one or more treatments having a number of orientations of the number of virtual teeth. As described herein, the virtual treatment process can include moving at least one of the number of physical teeth to clear an implant location for an optimal dental occlusion configuration.

The virtual treatment process can include placing an implant at the implant location once cleared of physical teeth. Additionally, the virtual treatment process can include positioning at least one of the number of physical teeth outside of the implant location to the optimal dental occlusion configuration while the implant location is healing.

In some embodiments, the virtual treatment process can include fabricating (e.g., forming) a removable dental positioning appliance (e.g., aligner) to implement each increment of the treatment. In various embodiments, the implant location (e.g., a landmark) can be incorporated into one or more of the removable dental positioning appliances.

Block 520 of FIG. 5 shows that one or more teeth can, in various embodiments, be moved (e.g., repositioned) using a first number of a series of dental appliances, from a first orientation to a second orientation, the second orientation exposing the implant location. For example, the implant location that is exposed by moving the one or more teeth to the second orientation can be the implant location determined based upon the virtual model, as described herein.

An implant can be placed at the exposed implant location using a landmark included in at least one of the series of dental appliances (e.g., aligners), as shown in block 530. In some embodiments, the landmark can be a simple indicator that, for example, when used in conjunction with the CT image, can direct the dentist or implant surgeon to an appropriate location for the implant. In some embodiments, the landmark can perforate the dental appliance and serve as a drill guide, or serve as an attachment for a separate drill guide, to enable determination of the angulation and/or depth of the implant to be built into the aligner itself.

In some embodiments, a layer of polymeric material at the site of the landmark may be thin, for example, such that attaching the separate drill guide can assist in providing a guide that reliably enables determination of the angulation and/or depth of the implant. Among various embodiments, the separate drill guide can, in some embodiments, be a cylinder with a circumferential groove forming part of a drill guide mating feature to receive, for example, an edge of a depression, a marking, a hole, a fixture, and/or an inset serving as a landmark.

As shown in block 540, one or more teeth can be repositioned using a second number of the series of dental appliances (e.g., aligners), from the second orientation to a successive orientation. That is, in some embodiments, after placing and/or positioning the implant at the desired location, the first of the second number of the series of aligners can be applied to the patient's teeth to continue repositioning of the teeth from the orientation in which the implant was placed and/or positioned to continue movement of the teeth to a final position.

In some embodiments of the present disclosure, the implant can be placed and/or positioned at the earliest exposing of the implant location. A dental appliance providing an earliest exposing of the implant location can include the landmark, in various embodiments, providing a guide for locating a position for the implant.

As described in the present disclosure, one or more teeth can be repositioned using the second number of the series of dental appliances while the patient is healing from implant placement. In some embodiments, the second number of the series of dental appliances can, in various embodiments, include an offset area corresponding to the implant. By including the offset area in a portion of at least one of the second number of the series of dental appliances, pressure on the location of the implant and/or surrounding tissue can be relieved in order to facilitate healing and osseointegration and/or improved recovery (e.g., reducing impaction trauma to the wound site).

In some embodiments, the second number of the series of dental appliances can, in various embodiments, be configured to have an abutment geometry for attaching a temporary tooth structure in the offset area. Hence, in some embodiments, the temporary tooth structure can, in various embodiments, be attached to the abutment geometry of one or more of the second number of the series of dental appliances.

In some embodiments, the offset area (e.g., included in at least one of the second number of the series of dental appliances) can, in various embodiments, be filled, lined, painted, or coated with tooth-colored material. A dental plan, as described in the present disclosure, can include restoring a tooth structure to the implant once the implant has osseointegrate and the neighboring teeth are repositioned to the desired dental occlusion arrangement. When the space created by the aligner is larger than the intended restoration shape at the implant site and the implant is integrated into the bone, the restoration can be placed as soon as the neighboring teeth have reached a stable position, even if additional orthodontic treatment is still to be preformed elsewhere in the patient's mouth.

Figure 6A:
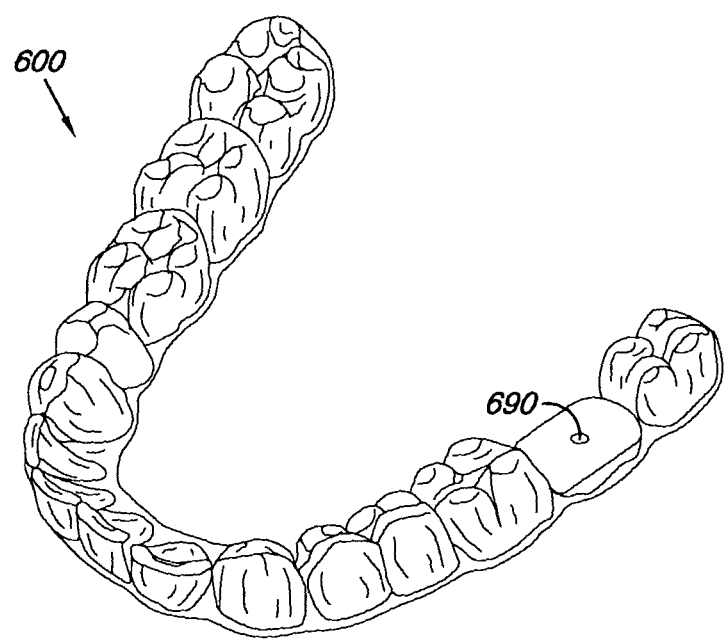
FIG. 6A illustrates a dental positioning adjustment appliance having an aperture for indicating an implant position according to an embodiment of the present disclosure.

FIG. 6A illustrates a dental positioning adjustment appliance having an aperture for indicating an implant position according to an embodiment of the present disclosure. In the embodiment of FIG. 6A, an appliance 600 includes an implant positioning indicator. In the embodiment of FIG. 6A, the indicator (e.g., a landmark) is an aperture 690 provided in the material used to form the appliance. Such apertures can be formed during fabrication of the appliance and/or after the fabrication is complete.

A treatment professional can, for example, view the area through the aperture to see whether the position of the aperture is in the correct anatomical location, and whether there will be enough room for the implant, among other suitable functions. The aperture can be of any suitable size and/or shape. In some embodiments, the aperture can be used to guide the placement of the implant in the indicated location through the aperture.

Additionally, as illustrated in the embodiment of FIG. 6A, the aperture 690 can be placed on a portion of the appliance that is flat. The appliance can have any suitable shape, such as a model tooth contour, a model or actual gum contour, and/or other suitable shapes.

In some embodiments, the appliance 600 can be used to anchor another type of indicator to be placed near the area in which the implant is to be positioned. For example, the indicator can be a wire measuring or pointing device or other type of pointing device that can be utilized to point to the area in which the implant is to be positioned or can be used to help provide measurement information to aid in positioning the implant.

Indicators may, for example, be a self-adhesive indicator, a clip-on indicator, a suction adhered indicator, a bonded indicator, a Velcro-affixed, or a snap-on indicator. However, the embodiments of the present disclosure should not be limited to such methods of attachment.

A wire or other radiopaque material can be beneficial, for example, because it can be viewed in an x-ray. However, the embodiments of the present disclosure should not be limited to such materials.

Figure 6B:
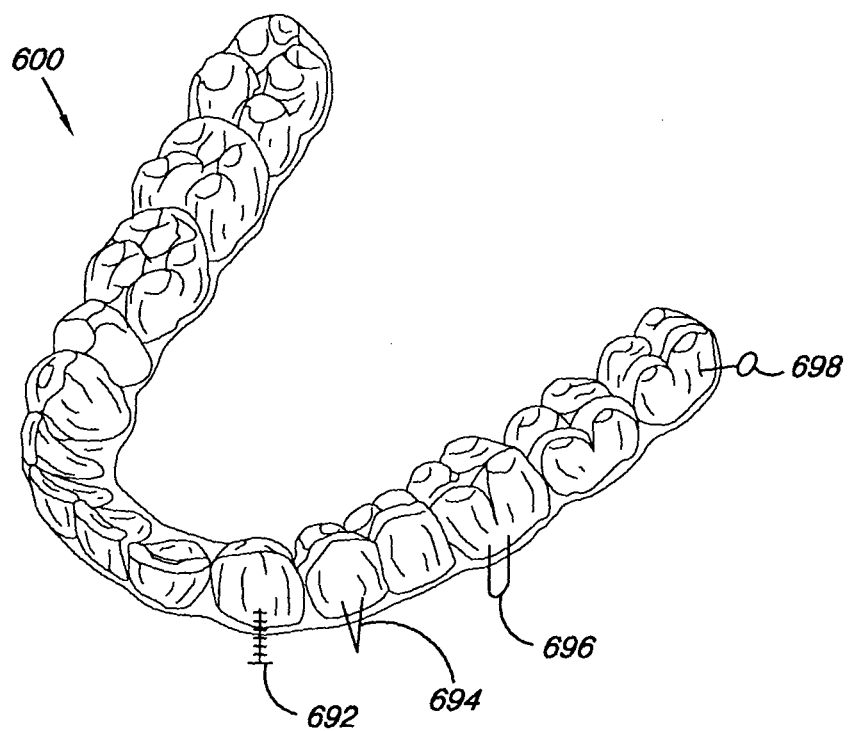
FIG. 6B illustrates a dental positioning adjustment appliance having a number of indicators positioned thereon according to an embodiment of the present disclosure.

FIG. 6B illustrates a dental positioning adjustment appliance having a number of indicators positioned thereon according to an embodiment of the present disclosure. Such indicators can be used for a variety of purposes. For example, such indicators can be used to identify to the clinician where to position an implant, or as a reference from which to determine where to place the implant.

The indicator may also contain a temporary ink or dye that, in some embodiments, can be transferred to the gum tissue to enable the clinician to visualize the desired location of the implant placement, or as a reference position indicator. Such indicators may be particularly useful for the placement of temporary anchorage devices (mini-implants), for example.

In the embodiment illustrated in FIG. 6B, for instance, several indicators are provided. Such indicators can be used as pointing devices that point to the area at which an implant is to be positioned.

Any suitable pointing device can be used in such embodiments. For example, suitable pointing devices can have various shapes and/or sizes, can be made from various materials, and/or can be visible on x-rays and/or via other scanning or photographing techniques, etc.

The indicators can also be placed proximally to (e.g., next to or attached to) the appliance in any suitable manner. A releasable adhesive is one such suitable manner for attachment and allows the indicator to be removed which may be beneficial in some embodiments.

In the embodiment of FIG. 6B, the appliance 600 includes indicators 692, 694, 696, and 698. Such indicators can provide different benefits based upon their shapes.

Such indicators may also contain rotating/pivot joints such that the position can be adjusted and/or locked, for example, while the desired position is being verified with radiographs. In some embodiments, there may also be telescoping or locking telescopic indicators to allow extension of the indicator to more easily locate the desire position, among other benefits.

For example, indicator 692 has a number of different points that can be used as reference such as the left end of the second line from the bottom. This can be helpful in pointing a more exact position.

Indicators 694, a pointer, and 696, a u shape, can provide a general directional orientation (e.g., a vertical versus horizontal alignment to provide that the implant can fit into the area for the implant when installed. Indicator 698 is a circle and as shown, can be used with a reference line.

The circle, for example, can allow for the treatment profession to locate where on the gingiva an implant may be positioned. Such embodiments can, for example be utilized where the clinician can affix the indicator to identify the desired position, mark the tissue through the loop, and then position the implant at the mark. In some embodiments, the implant can be placed directly through the loop. When used with a line, the line can be used to aid in correctly orienting the implant, among other uses for such a feature.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A method for positioning an implant, the method comprising:
   determining an implant location based on a virtual model of an optimized dental occlusion according to a treatment plan;
   moving one or more teeth of a plurality of teeth from a first orientation to a different second orientation according to the treatment plan using a number of appliances of a series of dental appliances formed to enable movement of the one or more teeth from the first orientation to the different second orientation, the second orientation exposing the implant location;

placing the implant at the exposed implant location using a particular one of the series of dental appliances comprising a shell that includes a plurality of cavities shaped to receive the plurality of teeth and having a landmark formed in the shell positioned to provide a guide for placing the implant at the exposed implant location; and moving the one or more teeth from the second orientation to a third orientation, that is different than the first and second orientations after the placement of the implant using the particular one of the series of dental appliances.

2. The method of claim 1, wherein placing the implant comprises placing the implant at the earliest exposing of the implant location.

3. The method of claim 1, wherein the method includes:
scanning in three dimensions a patient's initial dental anatomy; and
creating the virtual model of the optimized dental occlusion based on the patient's dental anatomy.

4. The method of claim 3, wherein the scanning includes:
digitally scanning the patient's dentition;
digitally scanning a dental structure including anatomical features affecting the implant location; and
superimposing the dental structure to the dentition of the 3-D patient scan.

5. The method of claim 3, wherein the method includes restoring a tooth structure to the implant upon osseointegration of the implant and achieving the optimized dental occlusion.

6. The method of claim 1, wherein the landmark is selected from a group including: a depression, a marking, a hole, a fixture, an inset, and a drill guide structure.

7. The method of claim 1, wherein the movement from the second orientation to a third orientation occurs during a healing period for osseointegration of the implant.

8. A method for dental virtual treatment planning, the method comprising:
planning a virtual treatment process for a plurality of virtual teeth of a virtual model that are modeled based on a plurality of physical teeth;
wherein a first increment of the virtual treatment process provides for moving at least one of the plurality of virtual teeth from a first configuration to a second configuration that is different than the first configuration to expose an implant location for enabling insertion of an implant;
wherein a second increment of the virtual treatment process provides for, after exposing the implant location, moving at least one of the plurality of virtual teeth outside of the implant location from the second configuration to a third configuration that is different than the first and second configurations;
fabricating a first dental appliance according to the virtual model to implement the first increment of the virtual treatment process; and
fabricating a second dental appliance according to the virtual model to implement the second increment of the virtual treatment process, the second dental appliance having:
a shell that includes a plurality of cavities shaped to receive the plurality of physical teeth and move at least one of the plurality of physical teeth outside of the implant location from the second configuration to the third configuration, and
a landmark formed in the shell positioned to provide a guide for placing the implant at the exposed implant location while the shell is worn over the plurality of physical teeth.

9. The method of claim 8, wherein the second increment of the virtual treatment process provides for the movement from the second configuration to a third configuration during a healing period for osseointegration of the implant.

10. A series of dental appliances comprising:
a number of the series of dental appliances formed to reposition one or more teeth from a first configuration to a second configuration according to a treatment plan, wherein the one or more teeth repositioned to the second configuration exposes an implant location; and
a particular one of the series of dental appliances comprising:
a shell that includes a plurality of cavities shaped to receive the plurality of physical teeth and move at least one of the plurality of physical teeth outside of the implant location from the second configuration to a third configuration that is different than the first and second configurations, and
a landmark formed in the shell positioned to provide a guide for placing an implant at the exposed implant location while the shell is worn over the plurality of physical teeth.

11. The series of dental appliances of claim 10, wherein the particular one of the series of appliances includes an offset portion formed as part of the dental appliance, comprising an abutment separating the shell a distance from the implant and surrounding tissue.

12. The series of dental appliances of claim 11, wherein the abutment provides a connection for attachment of a tooth-like object.

13. The series of dental appliances of claim 11, wherein the abutment enables attachment of a temporary tooth structure in the offset relief portion or wherein the particular one of the series of appliances includes a pontic geometry built into the offset relief portion.

14. The series of dental appliances of claim 11, wherein a top of the offset portion provides a base of a solid tooth-like object formed as part of the dental appliance shell.

15. The series of dental appliances of claim 10, wherein the landmark is selected from a group of landmarks including:
an aperture formed in the particular one of the series of appliances;
a pointing device provided proximal to the particular one of the series of appliances.

16. The series of dental appliances of claim 15, wherein the pointing device is attached to the particular one of the series of appliances.

17. The series of dental appliances of claim 10, wherein the landmark comprises an implant placement guide.

18. The series of dental appliances of claim 17, wherein the implant placement guide comprises a perforation in the shell.

19. The series of dental appliances of claim 17, wherein the implant placement guide comprises an insert that progresses partially or completely through the shell.

20. The series of dental appliances of claim 17, wherein the implant placement guide comprises an everted cylinder.

21. The series of dental appliances of claim 20, wherein the shell further includes a drill guide coupled to the everted cylinder.

22. The series of dental appliances of claim 17, wherein:
the shell generally conforms to, but is slightly out of alignment with the one or more teeth to move the one or more teeth during the healing period for osseointegration of the dental implant; and
wherein the successive configuration is based on an optimal dental occlusion including a pre-determined implant location.

23. The series of dental appliances of claim 17, wherein the implant placement guide comprises a landmark for positioning of the implant.

24. The series of dental appliances of claim 10, wherein at least a second dental appliance of the series of dental appliances includes an offset area corresponding to the implant.

25. The series of dental appliances of claim 24, wherein at least the second dental appliance of the series of dental appliances has an abutment geometry for attaching a temporary tooth structure in the offset area.

26. The series of dental appliances of claim 25, wherein the temporary tooth structure is attached to the abutment geometry.

27. The series of dental appliances of claim 24, wherein the offset area is filled with tooth-colored material.

28. The series of dental appliances of claim 10, wherein the movement from the second configuration to a third configuration occurs during a healing period for osseointegration of the dental implant that is intended to be placed at the exposed implant location.

\* \* \* \* \*